United States Patent [19]

Olsen

[11] Patent Number: 5,531,698

[45] Date of Patent: Jul. 2, 1996

[54] OPTICAL REFLECTION SYSTEMS AND METHODS FOR CASSETTE IDENTIFICATION FOR DRUG PUMPS

[75] Inventor: James M. Olsen, Plymouth, Minn.

[73] Assignee: SIMS Deltec, Inc., St. Paul, Minn.

[21] Appl. No.: 471,859

[22] Filed: Jun. 6, 1995

Related U.S. Application Data

[62] Division of Ser. No. 228,508, Apr. 15, 1994.

[51] Int. Cl.$^6$ .................................................. A61M 37/00
[52] U.S. Cl. .......................... 604/131; 604/151; 604/246; 604/67; 604/31; 128/DIG. 12; 128/ DIG. 13
[58] Field of Search ..................... 604/151–153, 604/250–254, 65–67, 50–30, 31–34, 131–132, 246; 128/DIG. 12, 13

[56] References Cited

U.S. PATENT DOCUMENTS

| | | |
|---|---|---|
| T 961,004 | 8/1977 | Horton . |
| 2,968,804 | 1/1961 | Buffington . |
| 3,555,286 | 1/1971 | Cote . |
| 3,777,165 | 12/1973 | Bryant et al. . |
| 3,985,133 | 10/1976 | Jenkins et al. . |
| 4,080,967 | 3/1978 | O'Leary . |
| 4,184,815 | 1/1980 | Casson et al. . |
| 4,280,136 | 7/1981 | Kashima et al. . |
| 4,311,377 | 1/1982 | Matteson . |
| 4,385,958 | 5/1983 | Long . |
| 4,557,725 | 12/1985 | Heyne et al. . |
| 4,559,038 | 12/1985 | Berg et al. . |
| 4,559,044 | 12/1985 | Robinson et al. . |
| 4,565,542 | 1/1986 | Berg . |
| 4,597,754 | 7/1986 | Thill et al. . |
| 4,601,702 | 7/1986 | Hudson . |
| 4,617,014 | 10/1986 | Cannon et al. . |
| 4,650,469 | 3/1987 | Berg et al. . |
| 4,652,260 | 3/1987 | Fenton Jr. et al. . |
| 4,671,792 | 6/1987 | Borsanyi . |
| 4,731,058 | 3/1988 | Doan . |
| 4,756,706 | 7/1988 | Kerns et al. . |
| 4,775,368 | 10/1988 | Iwatschenko . |
| 4,790,816 | 12/1988 | Sundblom et al. . |
| 4,799,381 | 1/1989 | Tromp . |
| 4,808,167 | 2/1989 | Mann et al. . |
| 4,818,186 | 4/1989 | Pastrone et al. . |
| 4,838,856 | 6/1989 | Mulreany et al. . |
| 4,838,857 | 6/1989 | Strowe et al. . |
| 4,842,584 | 6/1989 | Pastrone . |
| 4,847,990 | 7/1989 | Patrick . |
| 4,850,807 | 7/1989 | Frantz . |
| 4,856,339 | 8/1989 | Williams . |
| 4,878,896 | 11/1989 | Garrison et al. . |
| 4,927,411 | 5/1990 | Pastrone et al. . |
| 4,943,279 | 7/1990 | Samiotes et al. . |

(List continued on next page.)

FOREIGN PATENT DOCUMENTS

| | | |
|---|---|---|
| 0078645A1 | 5/1983 | European Pat. Off. . |
| 551088 | 7/1993 | European Pat. Off. . |
| 2262452 | 6/1993 | United Kingdom . |
| WO87/07161 | 12/1987 | WIPO . |

*Primary Examiner*—Randall L. Green
*Assistant Examiner*—Perry E. Van Over
*Attorney, Agent, or Firm*—Merchant, Gould, Smith, Edell, Welter & Schmidt

[57] ABSTRACT

The present invention concerns a pump provided with a control module and an attachable fluid reservoir cassette. The control module includes a pumping mechanism for pumping fluid from the fluid reservoir to the patient. The cassette is provided with appropriate indicia to identify differences between a plurality of cassettes. The control module further includes cassette indicia identification structure for identifying indicia on the cassette. One type of cassette identification system includes a projection extending from the cassette and structure associated with the control module which engages the projection. Another type of cassette identification system includes a light reflecting system which utilizes light from the control module and reflected off the cassette. Still other types of cassette identification systems utilize other non-contact switches or sensors to sense indicia on the cassette to identify the cassette from a plurality of cassettes.

10 Claims, 14 Drawing Sheets

U.S. PATENT DOCUMENTS

| | | |
|---|---|---|
| 4,950,244 | 8/1990 | Fellingham et al. . |
| 4,961,533 | 10/1990 | Teller et al. . |
| 4,978,335 | 12/1990 | Arthur, III . |
| 5,017,059 | 5/1991 | Davis . |
| 5,034,004 | 7/1991 | Crankshaw . |
| 5,047,014 | 9/1991 | Mosebach et al. . |
| 5,062,774 | 11/1991 | Kramer et al. . |
| 5,074,756 | 12/1991 | Davis . |
| 5,078,683 | 1/1992 | Sancoff et al. . |
| 5,082,014 | 1/1992 | Olichney . |
| 5,098,262 | 3/1992 | Wecker et al. . |
| 5,098,409 | 3/1992 | Stock . |
| 5,103,211 | 4/1992 | Daoud et al. . |
| 5,104,374 | 4/1992 | Bishko et al. . |
| 5,111,234 | 5/1992 | Taniguchi et al. . |
| 5,115,223 | 5/1992 | Moody . |
| 5,122,820 | 6/1992 | Pagano et al. . |
| 5,124,744 | 6/1992 | Ogura et al. . |
| 5,124,802 | 6/1992 | Ito et al. . |
| 5,207,642 | 5/1993 | Orkin et al. . |
| 5,211,626 | 5/1993 | Frank et al. . |
| 5,219,327 | 6/1993 | Okada . |
| 5,221,268 | 6/1993 | Barton et al. . |
| 5,244,463 | 9/1993 | Cordner, Jr. et al. . |
| 5,317,506 | 5/1994 | Coutre et al. . |
| 5,431,627 | 7/1995 | Pastrone et al. . |

OPTICAL REFLECTION SYSTEMS AND METHODS FOR CASSETTE IDENTIFICATION FOR DRUG PUMPS

This is a Division of application Ser. No. 08/228,508, filed Apr. 15, 1994, which application is incorporated herein by reference.

FIELD OF THE INVENTION

The present invention relates generally to drug pumps for pumping fluid to a patient. More particularly, the present invention relates to systems and methods for identifying attachable fluid cassettes which supply fluid to the drug pump for pumping to the patient.

BACKGROUND OF THE INVENTION

Various drug pumps are known for pumping fluid to a patient in connection with treatment of various medical conditions. Drug pumps are known which include a reusable control module with a disposable or reusable fluid reservoir cassette wherein the reservoir is either self-contained with the cassette or remote from the cassette. The control module pumps fluid from the cassette to the patient when the cassette is attached or mounted to the control module.

There is a need for using the control module in connection with different fluid reservoir cassettes. The cassettes may differ in the nature of the drugs or other fluid contained therein. Other differences might relate to the manner in which the fluid reservoir component cooperates with the control module to deliver the fluid to the patient. For example, the control module may include a pumping mechanism which engages a tube extending from the fluid reservoir cassette. The fluid reservoir cassettes may have variations in tubing size. In that case, it is important to identify to the control module the size of the tubing attached to the fluid reservoir cassette so that the proper amount of drug is delivered to the patient.

There is also a need for identifying a proper cassette from an improper cassette mounted to the control module. In some cases, the control module may be programmed or configured to pump fluid in a certain therapy from a particular cassette. If an improper cassette is mounted to the control module, there is a danger the patient may be given an improper drug.

There has arisen a need for systems and methods for identifying a fluid reservoir cassette which mounts to a control module of a drug pump.

SUMMARY OF THE INVENTION

The present invention relates to a pump including a control module having a control system with a processor and associated memory for controlling operation of the pump. The control system also includes a pumping mechanism for pumping fluid which is controlled by the processor. A fluid reservoir or cassette is selectively mountable to the control module. The fluid reservoir includes indicia for identifying a property of the fluid cassette such as tube size, drug type, or other. The control system includes structure for identifying the indicia associated with the fluid cassette. The structure for identifying indicia sends a signal to the processor indicative of the indicia sensed. An appropriate signal is generated for controlling the pumping mechanism or other pump function based upon the indicia identified. If an improper cassette is sensed, then a pump disabling program disables the pump mechanism from pumping even though the operator attempts to initiate the pumping operation.

In one preferred embodiment, the reservoir includes a base plate and a tube extending from the fluid reservoir which is interconnectable to the patient. The control module includes a pumping mechanism which engages the tube during pumping to move fluid from the reservoir to the patient.

There are various different indicia which may be provided on the base plate to identify a property of the reservoir. The base plate may include one or more projections. The structure for identifying indicia may include a force sensitive resistor mounted to the control module for engaging the projection on the base plate. The force sensitive resistor generates a signal for the processor of the control system.

Alternatively, the structure for identifying indicia may include a microswitch mounted to the control module which engages the projection on the base plate and sends a signal to the processor of the control system.

A further alternative for the structure for identifying indicia may include a slotted optical sensor and a reciprocally mounted plunger. The slotted optical sensor and the plunger are mounted to the control module. The plunger is engaged by the projection to move the projection relative to the optical sensor. The optical sensor generates a signal for the processor of the control system indicative of the change in position of the plunger.

In another alternative embodiment, the structure for identifying indicia may include a reciprocally mounted plunger which makes or breaks electrical connection between electrical contacts during engagement by the projection of the base plate. This electrical connection or disconnection generates a signal for the processor.

Instead of a mechanical interaction between indicia on the base plate and the structure for identifying the indicia associated with the control module, optics may be utilized wherein no contact between the control module and the cassette occurs with respect to the indicia identification structure. In one embodiment, the control module includes a light emitter for directing light toward the base plate. The indicia on the base plate includes an appropriately located prism arrangement for reflecting the light back toward the control module. The structure for identifying indicia further includes a light receiver for receiving the light reflected from the prism arrangement associated with the base plate and sending a signal to the processor.

Alternatively, the structure for identifying indicia may include a light emitter for directing light toward the base plate and the base plate may include a reflective patch for reflecting the light back toward the control module. The structure for identifying indicia further includes a light receiver for receiving the light reflected from the reflective patch and sending a signal to the processor.

Other cassette identification systems are usable including those relating to capacitive switches, Hall effect switches, reed switches, inductive switches, piezoelectric switches, magneto-resistive switches, and other non-contact switches. Acoustic switches are also usable. Also, optical print sensors may also be utilized for reading bar code information or the like printed on the cassette. Laser positioning sensors may be utilized where the height of a projection extending from the base plate is measured to identify the cassette.

The pump may include a display interconnected to the processor of the control system. Appropriate display programs are associated with the processor for generating an appropriate display depending on the cassette sensed by the control module. The pump apparatus may include an audible signal device for generating an appropriate audible signal when the control module has identified either a correct cassette or an incorrect cassette. Visual signals, such as a green and/or red LED, may be provided with the pump to indicate the appropriateness of the cassette sensed.

BRIEF DESCRIPTION OF THE DRAWINGS

FIGS. 21–23, 26, 27 and 29 show a control module and a first cassette. FIGS. 24 and 25 show a second cassette. FIG. 28 shows a third cassette.

DETAILED DESCRIPTION OF THE PREFERRED EMBODIMENTS

The present invention relates to systems and methods for automatically identifying a cassette mounted to a control module of a fluid pumping system, such as a drug infusion system. The identification system can identify indicia on the cassette relating to the type of drug, the concentration of the drug, the volume of the fluid reservoir, or the amount of drug pumped per activation of the pump, i.e., tube size. Such information is important to safe and effective drug therapy. When the information is entered automatically to the control module, such as with the indicia identifying system, a safer and more effective system results. There is less chance for human error, as would be the case if such information were entered manually. Also, the indicia identifying system can be used to prevent operation of the pump if an unauthorized cassette is attached.

Various cassettes are provided to be identified by the control module. The control module identifies the cassettes in one of a variety of manners, including engagement with a projection on the cassette or sensing optical signals or the absence of optical signals due to the presence of the cassette. Other structures and methods are provided to identify the cassettes.

Figure 1:
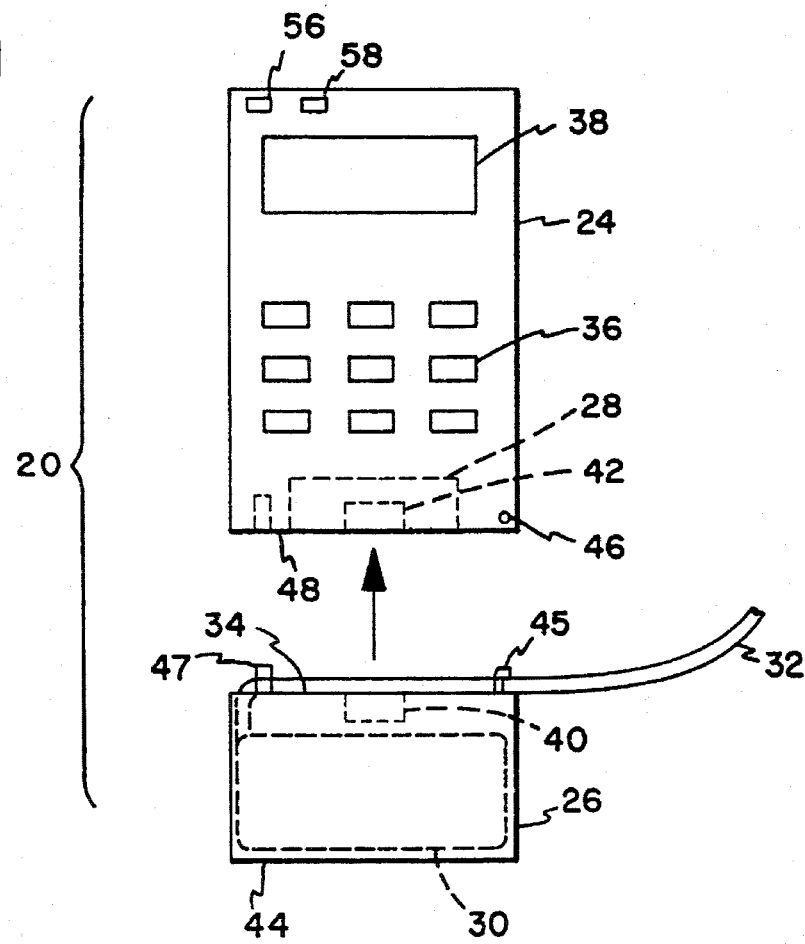
FIG. 1 is a schematic diagram of a pump apparatus according to the present invention, showing a self-contained fluid cassette separated from the control module.

Referring now to FIG. 1, a pump apparatus or pump 20 is shown. Pump 20 includes a control module 24 and a separate self-contained fluid cassette 26 which is mountable to the control module 24. Control module 24 is reusable. Cassette 26 may be disposable, or in some cases reusable after refilling. As will be discussed below in greater detail, cassette 26 can be configured as a remote reservoir adapter linking a remote fluid reservoir to control module 24.

One lock/latch mechanism for mounting cassette 26 to control 24 includes one or more hooks 45 which each engage a rod 46 mounted to control module 24. Loop 47 is grasped by loop engaging device 48 to releasably hold cassette 26 in place with hook 45 around rod 46. Other lock/latch mechanisms are anticipated for holding cassette 26 adjacent control module 24 to facilitate operation.

Control module 24 includes a pumping mechanism 28 which pumps fluid from cassette 26. Cassette 26 includes a fluid reservoir 30 with a compressible tube 32 extending therefrom. Tube 32 is interconnectable to the patient. Cassette 26 includes a base plate or pressure plate 34 having a top surface facing control module 24. Tube 32 is positionable between base plate 34 and pumping mechanism 28. Pumping mechanism 28 includes reciprocally mounted members which engage tube 32 in a particular manner to move fluid through tube 32. In one preferred embodiment, pumping mechanism 28 includes a reciprocally mounted inlet valve, a reciprocally mounted outlet valve, and a reciprocally mounted expulsor. The expulsor pushes fluid through the tube 32. The inlet and outlet valves, on opposite sides of the expulsor, open and close the tube to permit the passage of fluid through the tube 32. Pumping mechanism 28 includes a rotatable cam shaft controlled by a motor which moves the inlet and outlet valves and the expulsor in the appropriate manner. Base plate 34 and outer housing 44 cooperate to enclose reservoir 30 in FIG. 1. An example of one pumping mechanism useable in pump 20 is shown in U.S. Pat. No. 4,559,038, the disclosure of which is incorporated by reference.

Control module 24 further includes a plurality of keys 36 for providing input structure for the operator to input information into control module 24. Control module 24 also includes a display 38, such as an LCD (liquid crystal display) for displaying information to the operator. An audible signal device 56 may be provided to send an audible signal to the operator indicative of various conditions of pump 20. For example, a beeper may be provided for audible signal device 56. A visual signal device 58 may be provided for sending a visual signal to the operator indicative of various conditions of pump 20. For example, red and green LED (light-emitting diodes) may be provided for visual signal device 58.

Control module 24 includes a device 42 for identifying indicia 40 on cassette 26. Various cassette identification systems are anticipated including a variety of different identifying devices 42 and indicia 40.

Figure 2:
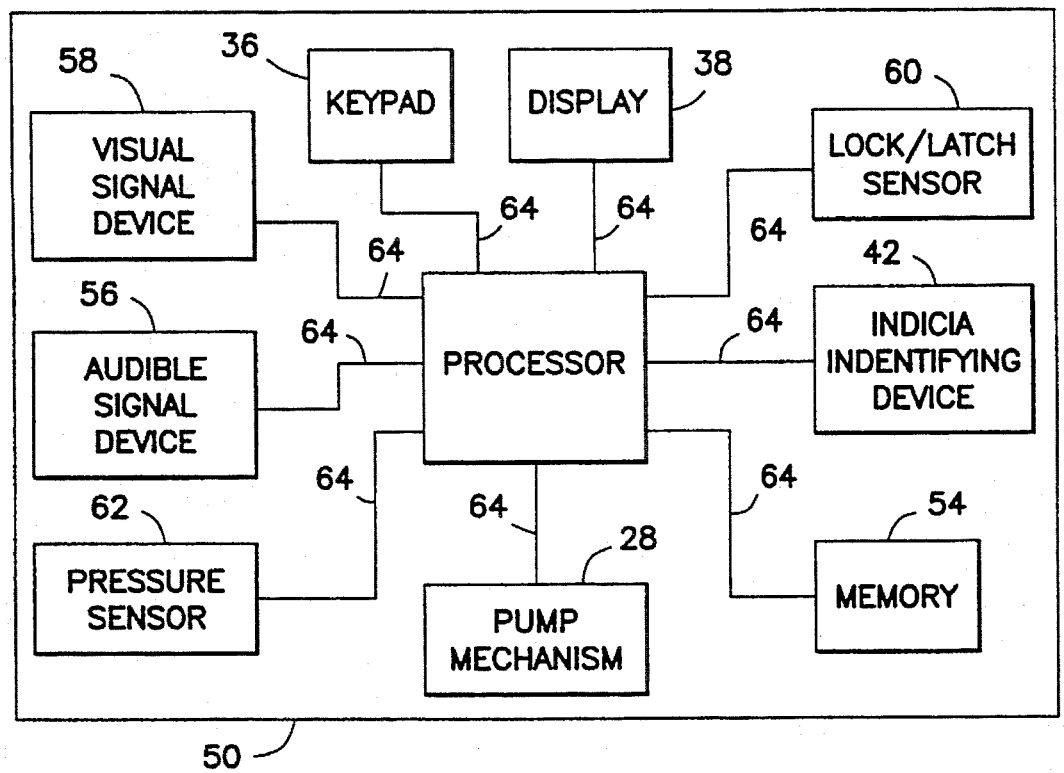
FIG. 2 is a schematic diagram of the control system of the control module shown in FIG. 1.

Referring now to FIG. 2, a control system 50 for control module 24 is shown. Control system 50 includes a processor 52 electrically interconnected to keypad 36, display 38, pump mechanism 28, and indicia identifying device 42. Audible signal device 56 and visual signal device 58 are interconnected to processor 52. Control system 50 further includes a memory 54 for storing various programs for operating pump 20. One program to be stored in memory 54 is pump disabling program for disabling pump mechanism 28 if an improper cassette is sensed.

FIG. 2 also shows a lock/latch sensor 60 interconnected to processor 52. Lock/latch sensor 60 senses when cassette 26 has been locked/latched to control module 24 through the operator activated latch structure 45, 46, 47, 48 which holds cassette 26 adjacent control module 24. FIG. 2 further shows a pressure sensor 62 interconnected to processor 52. Pressure sensor 62 is utilized to sense pressure in tube 32. Pressure sensor 62 and lock/latch sensor 60 are optional with respect to cassette identification. However, these sensors are used to advantage during cassette identification. These sensors can be utilized by processor 50 to identify if there happens to be a malfunction of the cassette identification system. Processor 52 will know when cassette 26 has been mounted to control module 24 by receipt of a lock/latch signal and an appropriate pressure signal (i.e., a pressure sensed within an acceptable operating range). At that point, processor 52 can begin looking for an appropriate signal from the identifying device 42 for identifying the indicia 40. If no identification signal is present, processor 52 does not permit initiation or continuation of the pumping operation by pump mechanism 28. Processor 52 may also send an appropriate error signal to display 38, audible signal device 56, and/or visual signal device 58. Processor 52 checks for a cassette identification signal periodically or continuously. Periodic is preferred as a manner of reducing energy consumption of pump 20.

In FIG. 2, the various sensors, switches, and other components of control system 50 are interconnected to processor 52 through interconnection link 64.

Figure 1A:
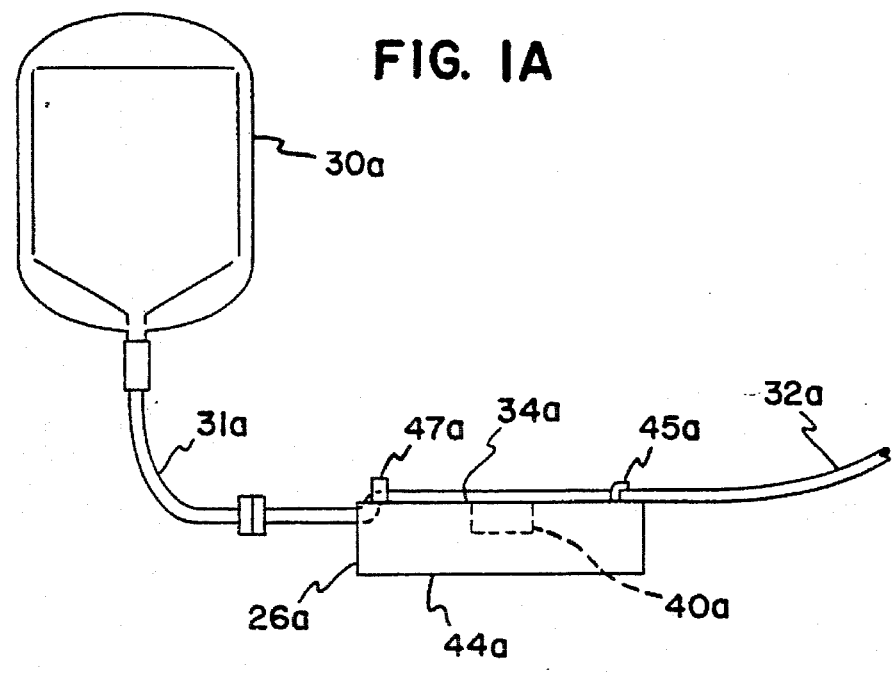
FIG. 1A is a schematic diagram of a remote reservoir adapter and remote fluid reservoir useable with the control module of FIG. 1.

Referring now to FIG. 1A, a remote reservoir adapter 26a is shown which is mountable to control module 24 in a similar manner as cassette 26. However, instead of including a self-contained fluid reservoir, adapter 26a is separate from remote fluid reservoir 30a. A tube 31a links remote fluid reservoir 30a to adapter 26a. Adapter 26a includes a base plate 34a with an extending base or housing 44a, hooks 45a, and a loop 47a. Housing 44a is smaller than housing 44 typically since no fluid reservoir is contained therein. Tube 32a extends from adapter 26a to be linked to the patient. As with respect to cassette 26, adapter 26a includes identifying indicia 40a to permit identification by control module 24.

In the following description of various preferred embodiments, reference to cassette 26 is to be interpreted as either cassette 26 of FIG. 1 or adapter 26a of FIG. 1A.

Figure 3:
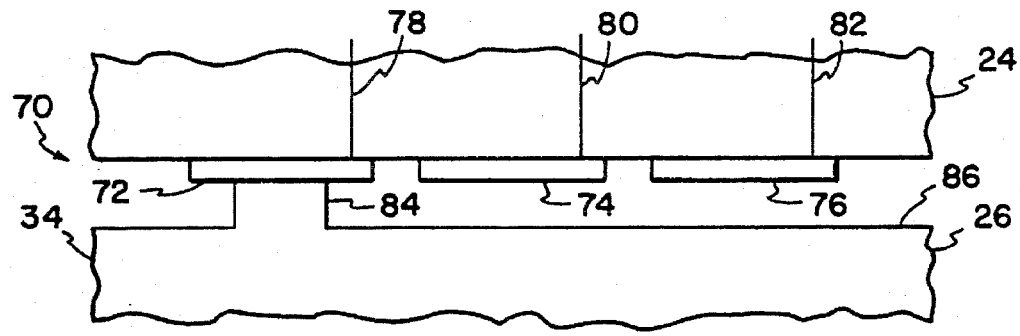
FIG. 3 is a first cassette identification system including a plurality of force-sensitive resistors.

Referring now to FIG. 3, a first cassette identification system 70 is shown including indicia associated with cassette 26 and indicia identifying structure associated with control module 24. The indicia on cassette 26 includes a projection 84 projecting upwardly from top surface 86 of base plate 34. The indicia identifying structure on control module 24 includes a plurality of force-sensitive resistors (FSRs). FSR 72 senses contact by projection 84. FSR 72 sends an appropriate signal through electrical connection 78 to processor 52 of control system 50.

As shown in FIG. 3, second FSR 74 and third FSR 76 are not engaged by any projections extending from cassette 26. Electrical connection 80 can send an appropriate signal from a second FSR 74 indicative of a condition where no projection is sensed. Similarly, electrical connection 82 can send a signal from third FSR 76 indicative of no projection sensed.

Cassette identification system 70 is capable of identifying at least three different cassettes 26. System 70 is shown identifying a first cassette 26. A second cassette could include a projection appropriately positioned to engage only second FSR 74. Similarly, a projection could be provided in the appropriate position to engage only third FSR 76. In this manner, a failure of one of the FSRs to sense the presence of a projection does not give an erroneous signal to processor 52.

If it is a desireable to identify more than three cassettes 26 utilizing only three FSRs, it is possible to utilize the FSRs in a manner which identifies up to eight different cassettes. However, it is not possible to differentiate between cassettes if one or more of the FSRs would happen to fail to identify a projection which is an engagement with the respective FSR, or if one of the projections is somehow damaged or malformed such that no engagement occurs. When only three different cassette sensors are provided, and only three cassettes are identified with them, then only one cassette projection is sensed. If no projection is sensed, or if more than one projection is sensed, then control module 24 recognizes an improper or damaged cassette has been attached.

Figure 4:
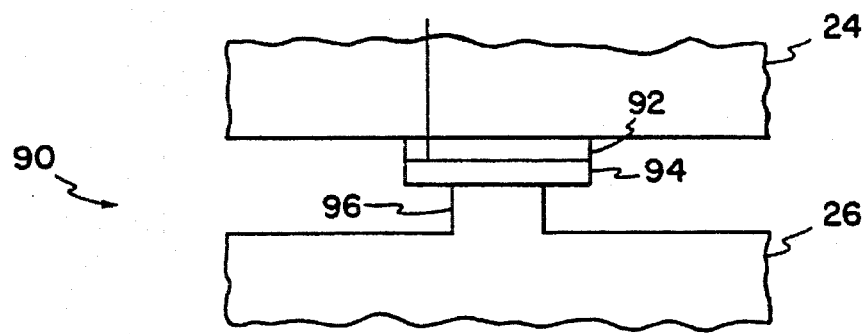
FIG. 4 is a second alternative cassette identification system including a force-sensitive resistor and an elastomer.

Referring now to FIG. 4, a second alternative cassette identification system 90 is shown. Like system 70, system 90 includes FSRs. In FIG. 4, FSR 94 is shown for sensing projection 96 extending from cassette 26. Compressible elastomer 92 is positioned between base surface 91 of control module 24 and FSR 94. Elastomer 92 provides a greater range of variation with respect to the height of projection 96 extending from cassette 26 relative to control module 24. Without elastomer 92, it may be possible for projection 96 to damage FSR 94 if projection 96 happens to extend too far from cassette 26 or if projection 96 is pushed too far into FSR 94. Similarly, if projection 96 does not extend far enough, FSR 94 will not sense the presence of projection 96 if there is insufficient contact below the threshold amount of the FSR or if there is no contact at all. Elastomer 92 extends the range of operation of FSR 94 such that variations in the height of projection 96 can be accommodated. Such accommodation is useful during manufacturing because the ranges on the possible height of projection 96 do not have to be as narrow as they might if no elastomer is present. Also, damage to the FSR may be avoided if the projection is pushed into the FSR at some point during mounting or dismounting of cassette 26.

Figure 5:
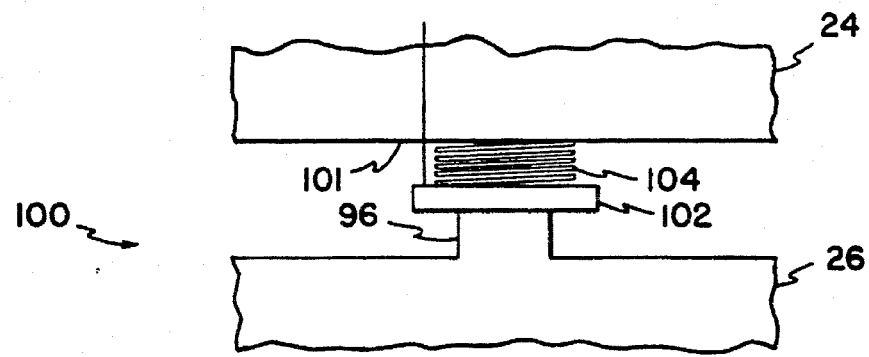
FIG. 5 is a third alternative cassette identification system including a force-sensitive resistor and a coil spring.

Referring now to FIG. 5, a third alternative cassette identification system 100 is shown. Instead of an elastomer 92 in system 90, system 100 includes a coil spring 104 which biases FSR 102 away from base surface 101 of control module 24. FSR 102 senses the presence of projection 106 extending from cassette 26. Spring 104 provides for an extended range in the height of projection 106 relative to control module 24. It will be appreciated that other types of springs, such as wavy, belleville and others could be used instead of coil spring 104.

Figure 6:
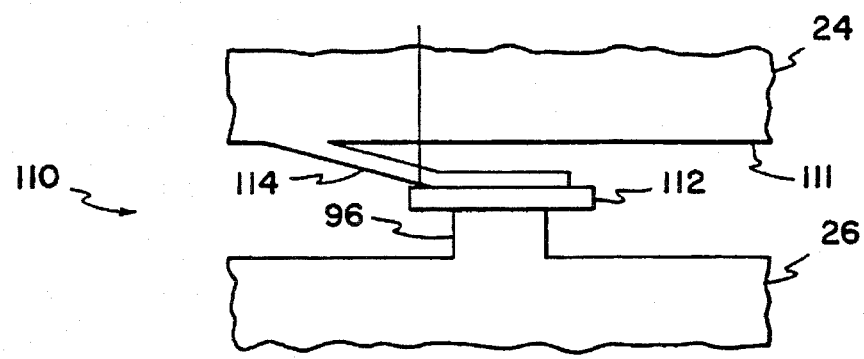
FIG. 6 is a fourth alternative cassette identification system including a force-sensitive resistor and a flexible beam.

Referring now to FIG. 6, a fourth alternative cassette identification system 110 is shown. Instead of an elastomer 92 as in system 90, or a spring 104 as in system 100, system 110 includes a flexible beam 114 extending from top surface 111 of control module 24. Flexible beam 114 positions FSR 112 at a spaced apart distance from top surface 111. FSR 112 senses the presence of projection 116. Flexible beam 114 accommodates variations in the extension of projection 116 relative to control module 24.

Figure 7:
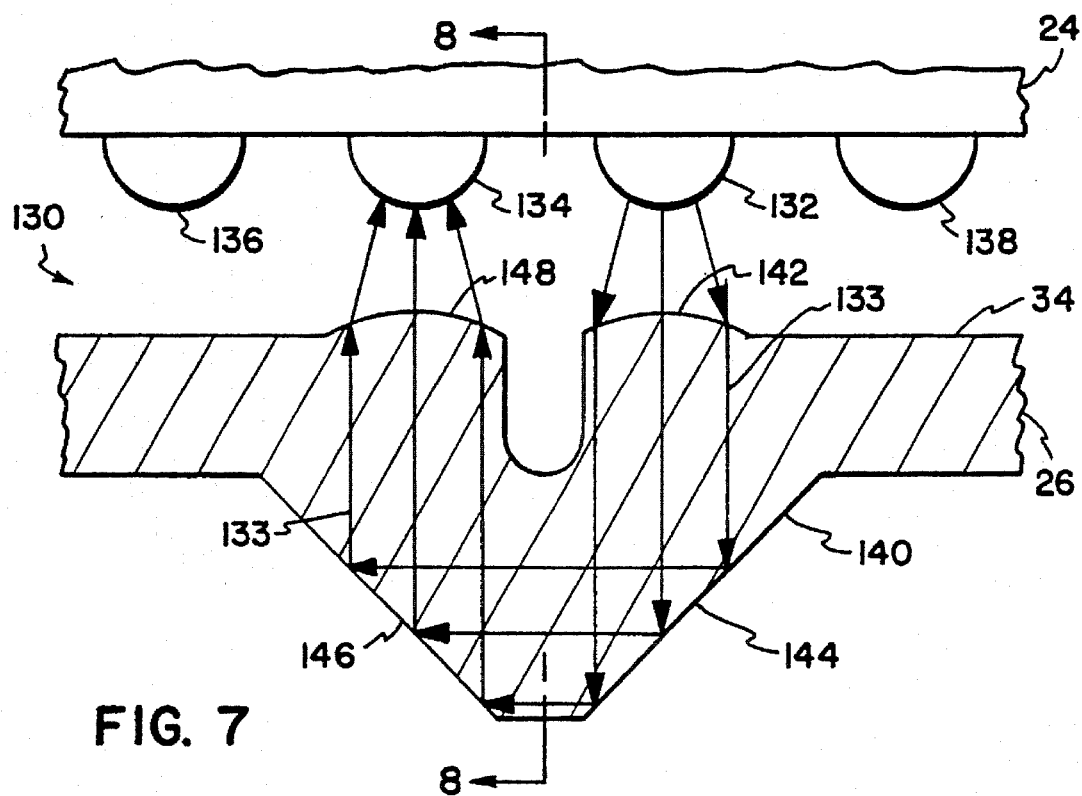
FIG. 7 is a fifth alternative cassette identification system including a prism arrangement.
Figure 8:
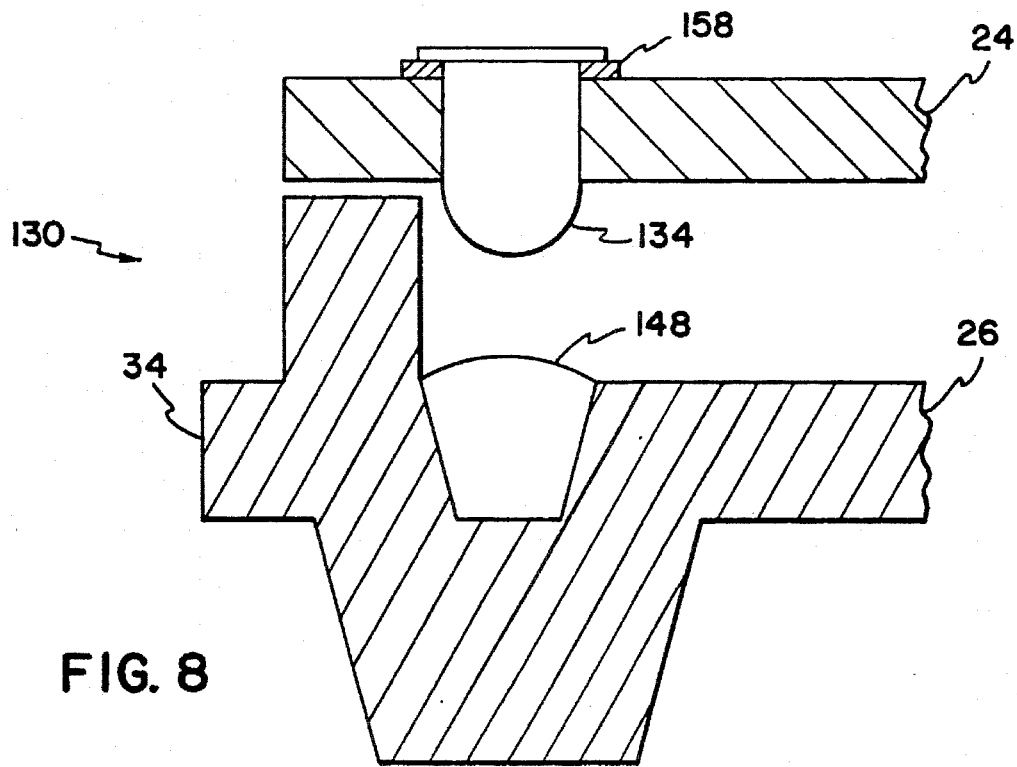
FIG. 8 is a cross-sectional view of the identification system shown in FIG. 7 taken along lines 8—8.
Figure 9:
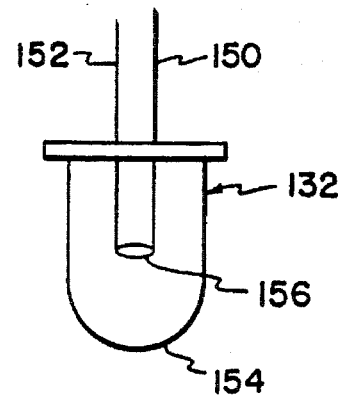
FIG. 9 is a view of the light emitter of the cassette identification system shown in FIGS. 7 and 8.

Referring now to FIGS. 7–9, a fifth alternative cassette identification system 130 is shown. Cassette 26 includes a prism arrangement 140 for reflecting light from control module 24 in an appropriate manner back toward control module 24 to identify cassette 26. Prism arrangement 140 includes a top surface 142, a first prism surface 144, a second prism surface 146, and a top surface 148. Base plate 34 is constructed to include prism arrangement 140 with the top surfaces 146, 148 forming a top surface portion of base plate 34 and surfaces 144, 146 forming a bottom surface portion of base plate 34.

Light emitter 132 emits light represented by arrows 133 which enters prism arrangement 140 and is reflected back toward control module 24. As shown in FIG. 7, prism arrangement 140 is reflecting light from emitter 132 to receiver 134. Receiver 134 sends an appropriate signal to processor 52 indicative of the presence of prism arrangement 140 reflecting light to receiver 134. Base plate 34 of cassette 26 is made from a material which permits the passage of light from emitter 132 to be reflected internally at surfaces 144 and 146. In one preferred embodiment, base plate 34 is made from polycarbonate which has an index of refraction of about 1.6 relative to air. Angles of 45 degrees relative to the direction of light passage are utilized for surfaces 144 and 146 in order to obtain sufficient internal reflection to have receiver 134 sense light being emitted from emitter 132.

To indicate the presence of a second cassette different from cassette 26, prism arrangement 140 is provided with a different configuration. Receiver 136 is utilized instead of receiver 134. In order to have receiver 136 receive light from emitter 132, surface 146 is moved adjacent (below in FIG. 7) receiver 136. Surface 144 would remain in the same location that is depicted in FIG. 7. Receiver 136 would send an appropriate signal to processor 52 indicative of the presence of prism arrangement 140 reflecting light to receiver 136.

To indicate the presence of a third cassette, receiver 138 is utilized. In order to have receiver 138 sense light from emitter 132, surface 144 is positioned in a reverse direction to reflect light from emitter 132 toward receiver 138. Surface 146 is appropriately positioned beneath receiver 138. In this manner, three different cassettes can be sensed by control module 24.

As shown in FIG. 7, top surface 142 is configured as a lens surface for columnating the light from emitter 132. As shown in FIGS. 7 and 8, top surface 148 is also configured as a lens for focusing the light passing through base plate 34 toward receiver 134.

Receivers 134, 136, 138 can be any of a variety of light receivers which generate a signal when light is present. Receivers 134, 136, 138 may be phototransistors, photodiodes, or photodarlingtons.

Referring to FIG. 9, an example of an emitter 132 is shown in greater detail. Emitter 132 may be an infrared emitting diode. An epoxy coating 154 encloses chip 156 which emits the infrared light. Extending from emitter 132 are two leads 150, 152 to connect to processor 52.

In cassette identification system 130, a comparitor circuit is useful for comparing the signals from all three receivers 134, 136, 138. It is preferred that the three receivers, 134, 136, 138 each generate a signal, with one signal being strong and two being weak. The comparitor circuit identifies the receiver with the stronger signal as being the receiver positioned in the appropriate manner relative to the prism arrangement 140 for identification of the cassette. The two weaker signals indicate that some light is reaching the receivers, but that light is not intended to cause those receivers to indicate the presence of the prism arrangement 140. The light that is being received by receivers 136, 138 which generates the weaker signals could come from emitter 132. Also, the light could come from external of pump 20.

One preferred cassette identification system 130 may include a modulating signal with respect to emitter 132. The light would preferably flash at a frequency not commonly found in the environments where pump 20 is to be used. This would increase the accuracy of cassette identification system 130. The modulating signal set at the uncommon frequency would help reduce inaccurate results caused by sunlight, room lighting, or other lighting devices which produce light which could hit pump 20, possibly causing an inaccurate reading of the cassette identification system.

Figure 10:
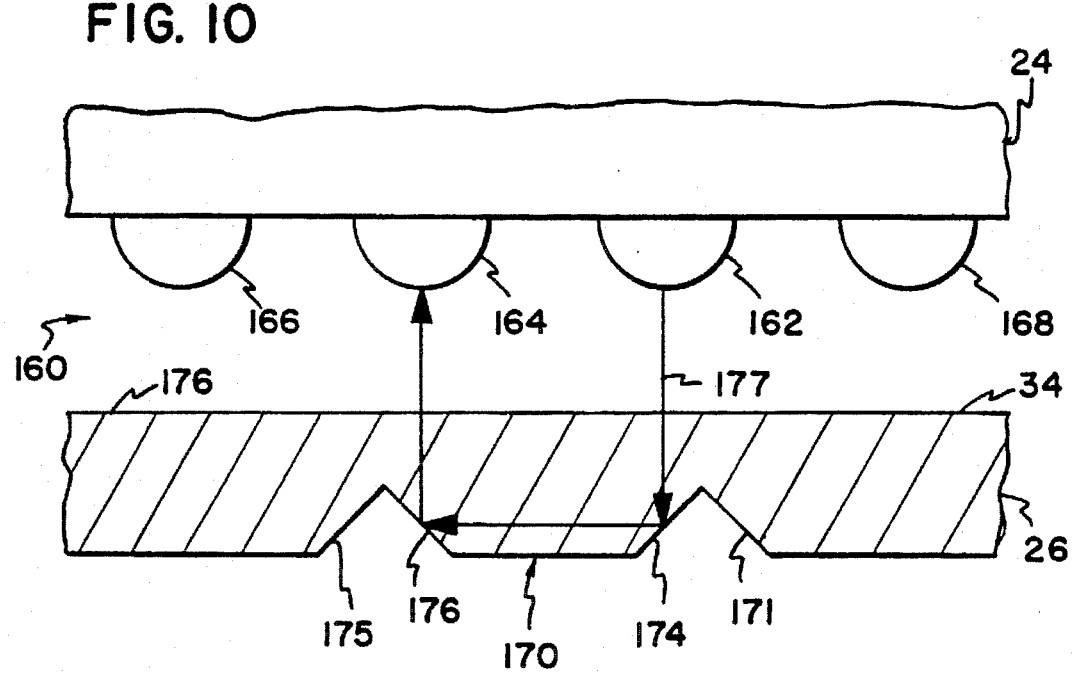
FIG. 10 is a sixth alternative cassette identification system including an alternative prism arrangement.

Referring now to FIG. 10, a sixth alternative cassette identification system 160 is shown. Control module 24 in FIG. 10 is similarly arranged as control module 24 of FIGS. 7 and 8. An emitter 162 is provided for directing light toward cassette 26. Cassette 26 includes structure for reflecting the light back toward control module 24. In particular, base plate 34 of cassette 26 includes a prism arrangement 170 which has a plurality of indentations. A first indentation 171 includes a first prism surface 174. A second indentation 175 provides a second prism surface 176. As shown in FIG. 10, light, represented by arrow 177, is emitted by emitter 162, passes through top surface 172 of base plate 34, and is reflected by first prism surface 174 toward second prism surface 176. Second prism surface 176 reflects the light back toward receiver 164.

As shown in FIG. 10, prism arrangement 170 is not directing light toward either second receiver 166 or third receiver 168. These receivers are utilized to identify different cassettes from cassette 26. A different prism arrangement 170 would be provided to reflect light from emitter 162 to receiver 166. In particular, indentation 175 and second prism surface 176 would be positioned beneath second receiver 166. Similarly, prism arrangement 170 would be modified in order to direct light from emitter 162 to third receiver 168 in order to identify a third cassette. In particular, indentation 171 and indentation 175 would be provided in a manner that first prism surface 174 and second prism surface 174 would direct light from emitter 162 toward receiver 168.

In cassette identification system 160, a comparitor circuit is useful for comparing the signals from all of the receivers 164, 166, 168. This identifies the stronger signal which is associated with the prism arrangement 170 directing light toward a particular receiver for cassette identification.

In an alternative arrangement (not shown) to the systems 130 and 160 of FIGS. 7–10, three emitters and one receiver could be provided. In that case, the emitters are switched on and off at different times and a comparitor circuit compares the signal received at the receiver from each emitter to identify which cassette 26 is being identified.

Figure 11:
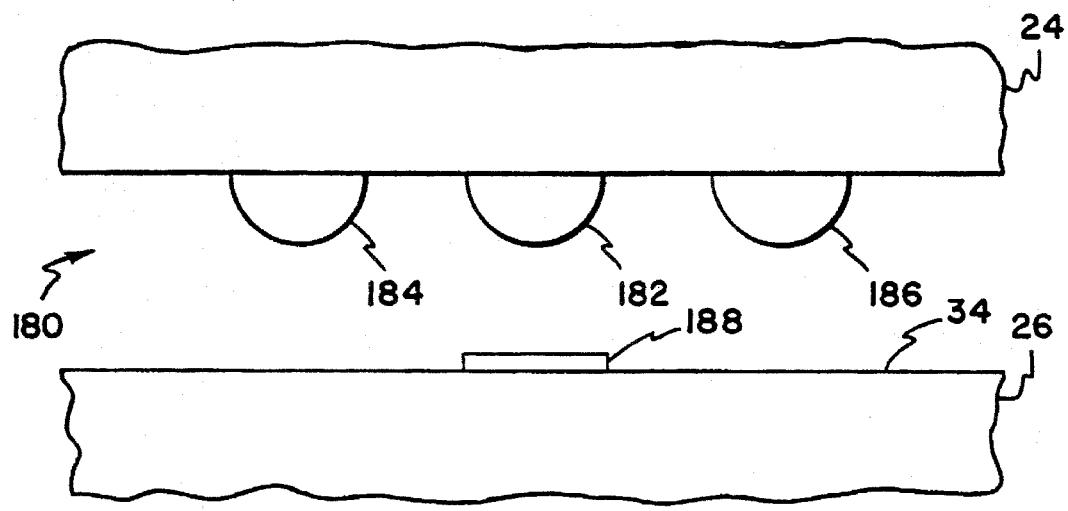
FIG. 11 is a seventh alternative cassette identification system including a reflective patch.

Referring now to FIG. 11, a seventh alternative cassette identification system 180 is shown. Instead of a separate emitter and receivers, system 180 includes three components 182, 184, and 186, which each function as an emitter of light and a receiver of light. Cassette 26 is provided with a reflective patch 188 for reflecting light back toward control module 24. Reflective patch 188 is appropriately positioned to reflect light back at one of the emitter/receiver components 182, 184, 186. In this case, patch 188 is below emitter/receiver component 182. The system 180 of FIG. 11 requires that reflective patch 188 be appropriately positioned during manufacturing. Base plate 34 reflects light, but in a different amount from reflector 188. It is not necessary that reflector 188 reflect more light than base plate 34.

An advantage of system 130 shown in FIGS. 7–9, and system 160 shown in FIG. 10 is that base plate 34 is molded with the appropriate configuration concerning the prism arrangement. No additional steps of placing a component or part on cassette 26 is needed with respect to systems 130, 160.

In cassette identification system 180, a comparitor circuit is useful for comparing the signals from the receivers of all three components 182, 184, 186. This identifies the stronger (or weaker) signal which is associated with the component positioned adjacent reflective patch 188.

Figure 12:
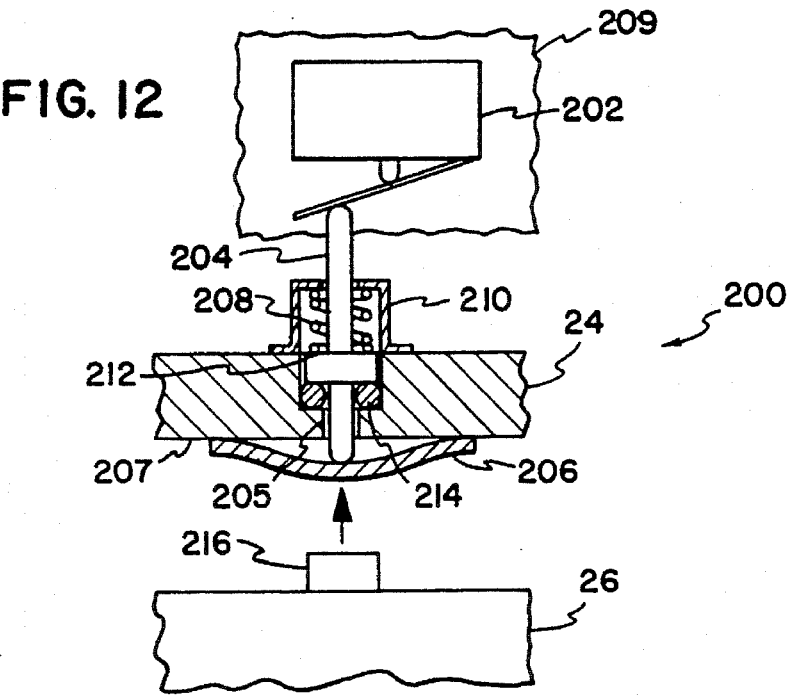
FIG. 12 is an eighth alternative cassette identification system including a microswitch.

Referring now to FIG. 12, an eighth cassette identification system 200 is shown. A microswitch 202 is activated when projection 216 moves plunger 204. Plunger 204 is positioned in opening 205 through chassis 207 of control module 24. A rubber boot 206 closes opening 205 from contaminants. Spring 208 biases plunger 204 away from microswitch 202. Spring 208 is positioned between spring retainer 210 mounted to chassis 207 and flange 212 of plunger 204. A seal 214 seals opening 205 from contaminants entering an interior of control module 206. Seal 214 and boot 206 serve similar functions in keeping contaminants out of control module 26. As such, it is anticipated that only one is needed.

Microswitch 202 is preferably adjustably mounted to board 209. Board 209 is mounted to chassis 207. Board 209 is useful for mounting other pump circuit components. An adjustable mounting permits adjustability of switch 202 such that the anticipated range of motion of plunger 202, including the various tolerances of projection 216, can be accommodated for during assembly and use such that consistent operation is achieved.

Figure 13:
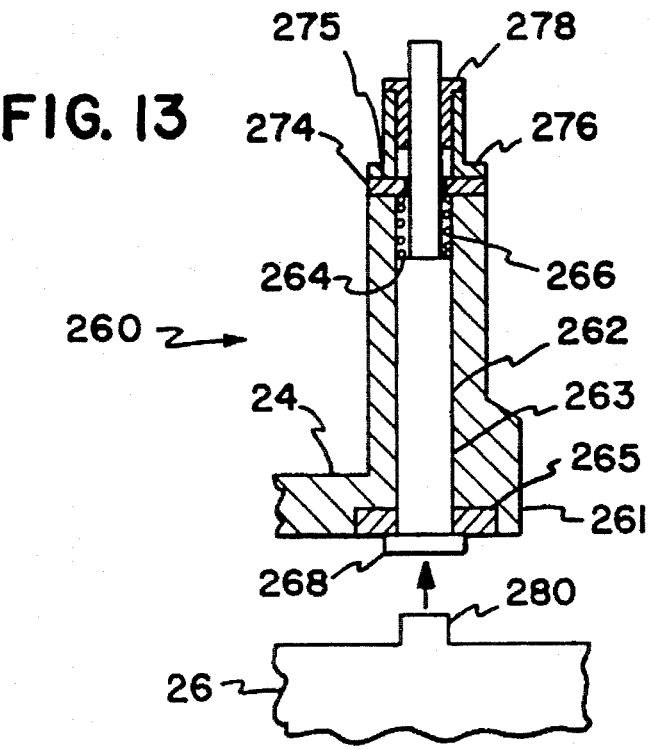
FIG. 13 is a ninth alternative cassette identification system including a reciprocally mounted plunger with an electrical contact thereon.

Referring now to FIG. 13, a ninth alternative cassette identification system 260 is shown. A plunger 262 is reciprocally mounted in aperture 263 in chassis 261 of control module 24. Plunger 262 is spring biased by spring 266 toward the position shown in FIG. 13. Seal 265 seals control module 24 from contaminants that come in contact with control module 24. Seal 265 also biases plunger 262 to the position shown in FIG. 13. Spring 266 is positioned between flange end 264 and spring retainer 274. When projection 280 engages flange cap 268 such that plunger 262 is moved upwardly, electrical contact is broken between upper contact 276 and a lower contact 275 located on spring retainer 274. Alternatively, electrical contact can be made when plunger 262 is moved upwardly toward a contact positioned above upper contact 276. Cap 268 is pressed into foam seal 270 in this position. An insulator 278 is press fit on an end of plunger 262. Insulator 278 is positioned between plunger 262 and upper contact 276 to insulate plunger 262.

Figure 14:
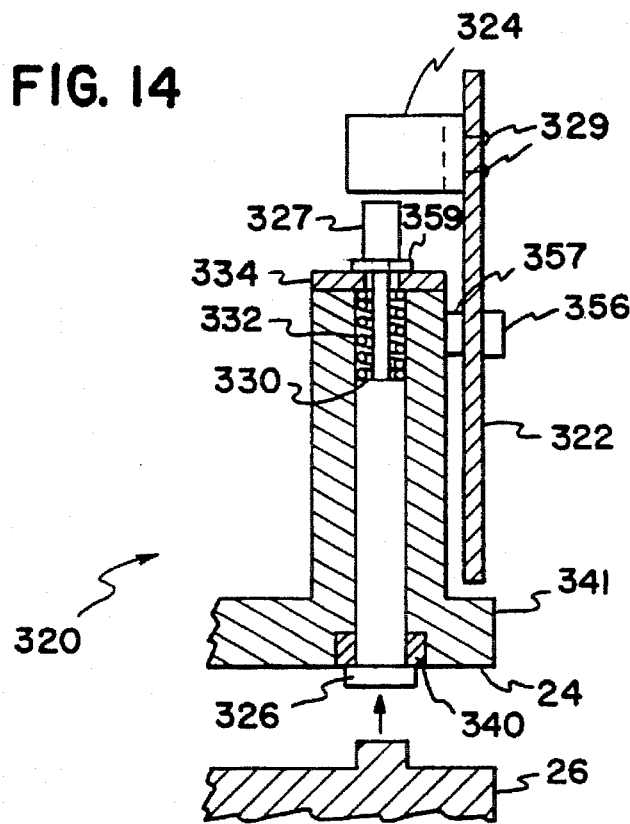
FIG. 14 is a tenth alternative cassette identification system including a slotted optical sensor and a reciprocally mounted plunger.
Figure 15:
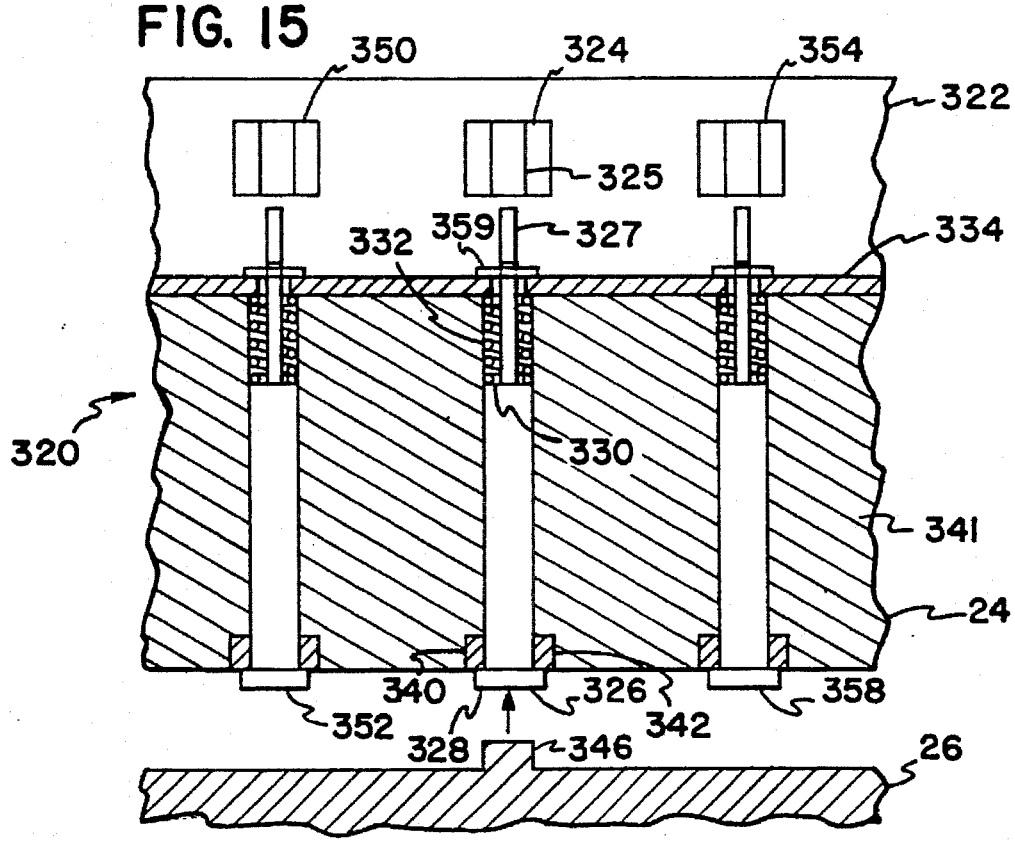
FIG. 15 is a side view of the cassette identification system shown in FIG. 14, showing three slotted optical sensors and three reciprocally mounted plungers.

Referring now to FIGS. 14 and 15, a tenth alternative cassette identification system 320 is shown. The cassette identification system 320 includes a board 322 positioned in an interior of control module 24. Mounted to board 322 are three slotted optical sensors 324, 350, 354. The optical sensors 324, 350, 354 may be soldered to board 322 at pins 329. The optical sensors are electrically connected to the processor of the control module. Board 322 is used for mounting various other circuit components of pump 20. Board is mounted to chassis 341 of control module 24 with at least one bolt 356 and a spacer 357. Pins (not shown) inserted into board 322 and chassis 341 may be used to achieve greater accuracy in mounting board 322 to chassis 341 during manufacturing.

In FIGS. 14 and 15, each optical sensor 324, 350, 354 is identical. Sensor 324 includes a light emitter on one side of slot 325 and a receiver on the opposite side of slot 325. Sensor 324 sends an appropriate signal to the processor of the control module indicative of whether, or to what degree, light from the emitter is being received by the receiver of sensor 324.

In system 320, three plungers 326, 352, 358 are reciprocally mounted to chassis 341. Plungers 326, 352, 358 are shown in a first position in FIGS. 14 and 15. In the first position, the path between the emitter and the receiver of each optical sensor is unobstructed. In some cases, the end of the plunger may be partially received by the sensor in the first position. In that case, the light path between the emitter and the receiver in the first position is less obstructed than in a second position. In one preferred embodiment, a higher voltage signal is sent to the processor of the control module when the plunger is in the fist position than when the plunger is in the second position.

In the system of FIGS. 14 and 15, slot 325 of optical sensor 324 receives an end 327 of plunger 326 when plunger 326 is moved upwardly to a second position. In the second position, the path between the emitter and the receiver is at least partially obstructed (or more obstructed than the first position). In one preferred embodiment, a lower voltage signal is sent to the processor of the control module than when the plunger is in the first position. Alternatively, the light path can become less obstructed when plunger 326 is moved by the projection to the second position.

Extending from the base plate 348 of cassette 24 is a projection 346 which engages an end 328 of one of the plunger 326 to move that plunger from the first position to the second position when cassette 26 is mounted to control module 24. An appropriately positioned projection 346 can be used to identify that cassette from one or more other cassettes which are not provided with a projection. The processor of control module 24 looks for the optical sensor sending the lower voltage signal indicative of the presence of a particular plunger in the second position. Preferably, although not required, control module 24 looks for a single projection. Identification of one, two or three projections may be used to identify up to eight cassettes, if desired.

Plunger 326 is spring biased away from the respective optical sensor 324 by spring 332 and seal 340. Spring 332 is positioned between spring retainer 334 mounted to chassis 341. A flange 330 is provided on plunger 326 to trap spring 332 between spring retainer 334 and flange 330. Chassis 341 further includes a recess 342 for receipt of seal 340. Seal 340 may be a foam seal for preventing moisture from entering the inside of the control module 24.

Plunger 326 can be made from round stock. End 327 is flattened to an appropriate width to be received by slot 325 of slotted optical sensor 324. A C-clip 359 limits each of the plungers 326 from moving too far away from the optical sensors 324. A groove or notch may be provided on plunger 326 to hold C-clip from axial movement along the plunger.

Figure 16:
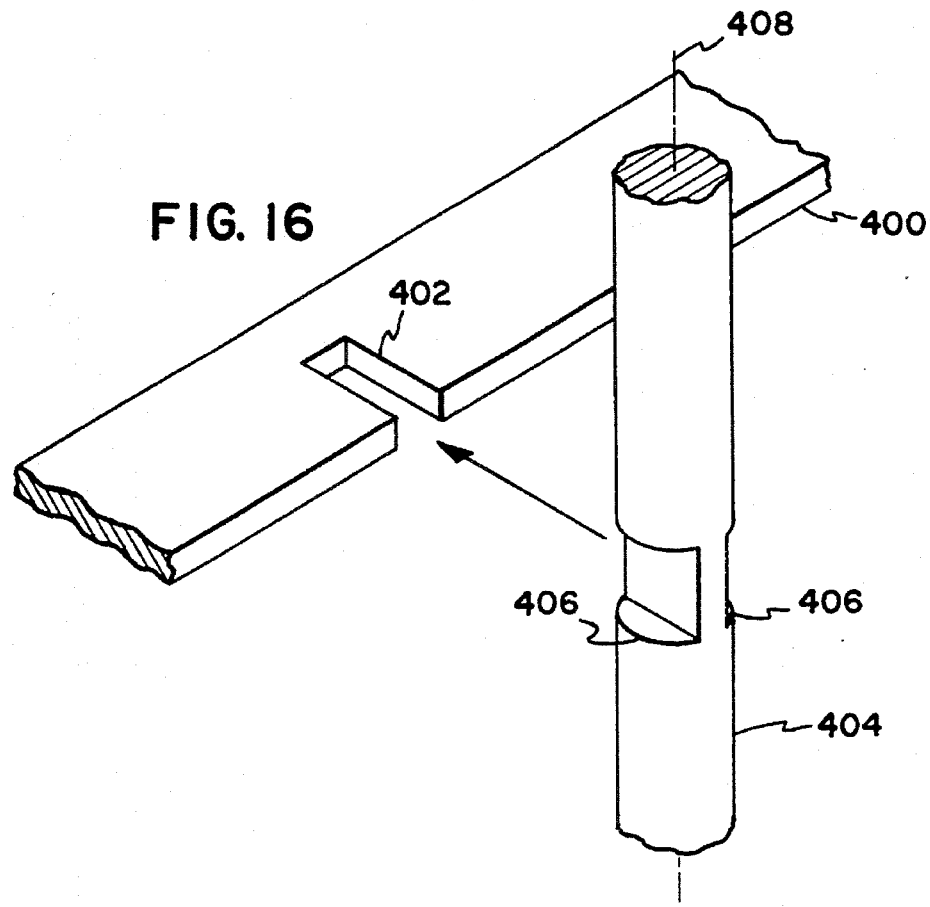
FIG. 16 is a second alternative plunger arrangement to the arrangement shown in FIGS. 14 and 15.

Referring to FIG. 16, a second alternative plunger arrangement is shown. Spring retainer 400 is provided with a slot 402 instead of an opening as in spring retainer 334. Plunger 404 is provided with a notch 406. The length of notch 406 along the longitudinal axis 408 of plunger 404 defines a range of possible movements of plunger 404.

Figure 17:
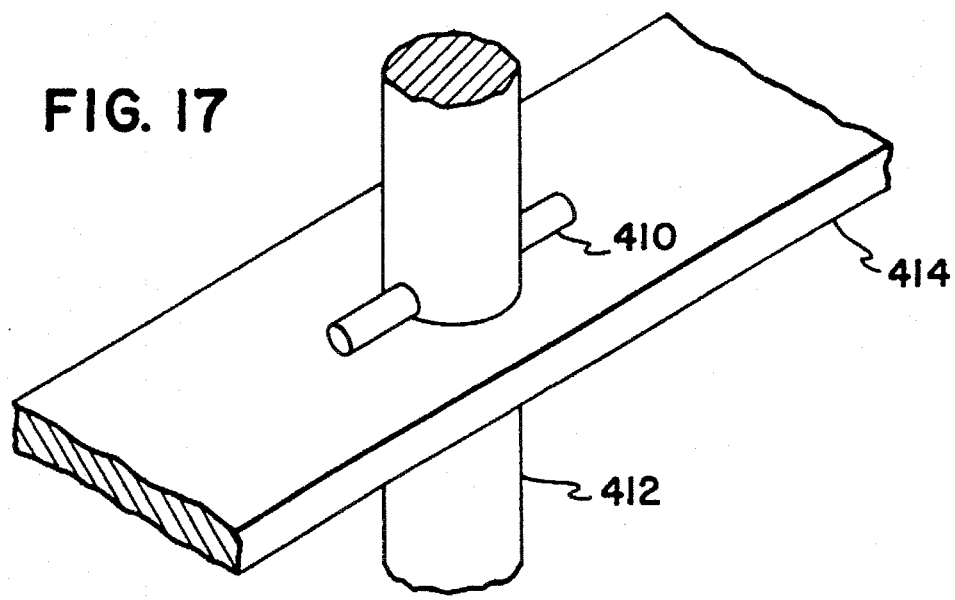
FIG. 17 is a third alternative plunger arrangement to the arrangement shown in FIGS. 14 and 15.

Referring to FIG. 17, a third alternative plunger arrangement is shown. Instead of a C-clip 359, a pin 410 is inserted through plunger 412. Pin 410 engages spring retainer 414 to limit movement of plunger 412.

Figure 18:
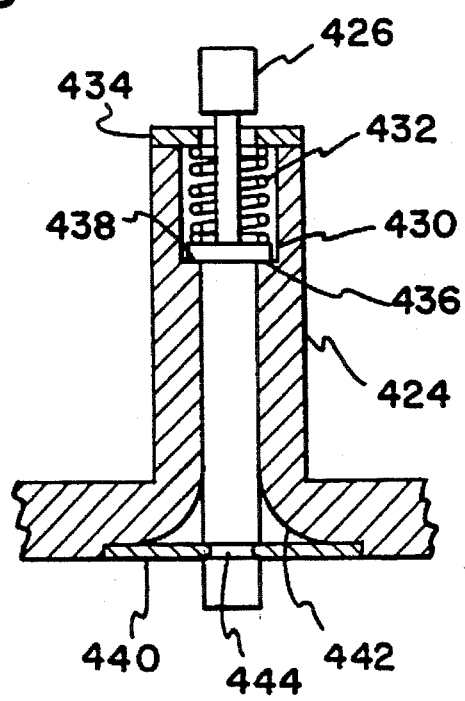
FIG. 18 is a fourth alternative plunger arrangement to the arrangement shown in FIGS. 14 and 15.

Referring to FIG. 18, a fourth alternative plunger arrangement is shown. A flange 430 is provided on plunger 426 to trap spring 432 between spring retainer 434 and flange 430. A stop surface 436 on plunger 426 engages stop surface 438 on chassis 424 to limit the distance plunger 426 can be biased away from the optical sensor. Chassis 424 further includes a recess 442 permitting receipt of seal 440 when plunger 426 is moved toward the optical sensor. A groove 444 is provided on plunger 426 to hold seal 440 in an appropriate position.

Figure 19:
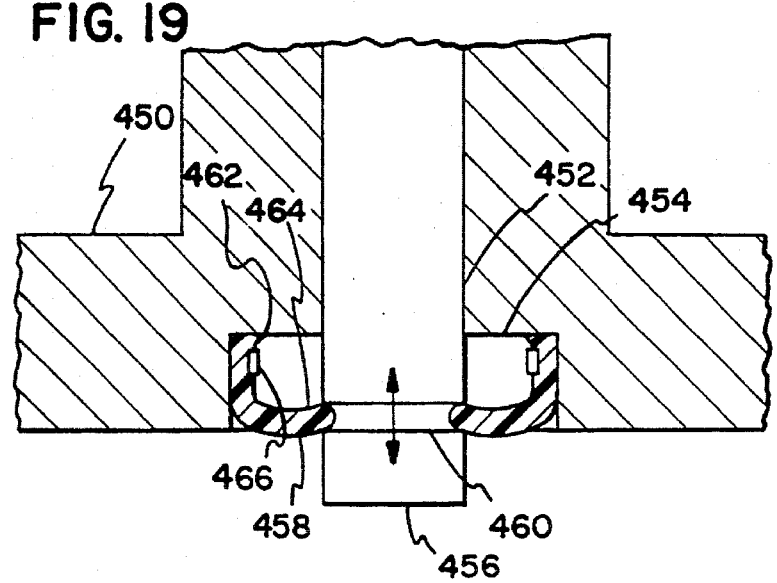
FIG. 19 is a fifth alternative plunger arrangement to the arrangement shown in FIGS. 14 and 15.

Referring now to FIG. 19, a fifth alternative plunger arrangement is shown. Plunger 452 is mounted to chassis 450 wherein a resilient silicon seal 458 seals the opening in chassis 450 for plunger 452. Seal 458 fits in recess 454. A metal ring 466 helps hold first end 462 of seal 458 in the position shown. Second end 464 of seal 458 holds plunger 456 in recess 460. As plunger 456 is moved up and down during use, such as in system 220 as shown in FIGS. 14 and 15, second end 464 moves with plunger, thereby effectively sealing the opening in the chassis.

Figure 20:
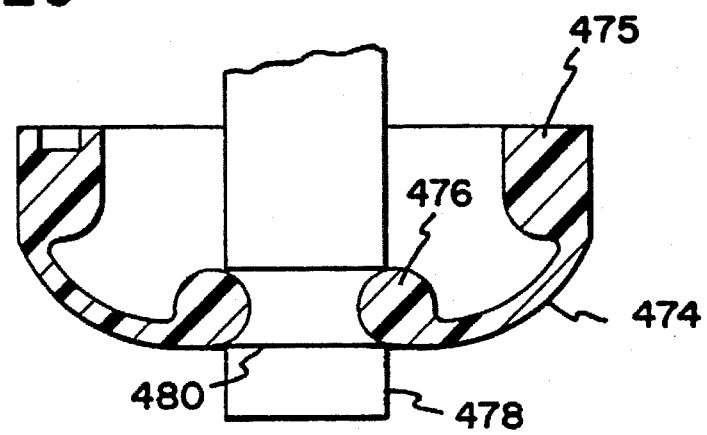
FIG. 20 is a sixth alternative plunger arrangement to the arrangement shown in FIGS. 14 and 15.

Referring now to FIG. 20, a sixth alternative plunger arrangement is shown. Instead of seal 458 of FIG. 19, seal 474 is provided for sealing the opening in the chassis for plunger 478. First end 475 of seal 474 engages the chassis. A second end 476 engages a recess 480 in plunger 478. Second end 476 of seal 474 moves with plunger 478 as plunger 478 moves up and down during attachment and detachment of cassette 26.

FIGS. 3-20 illustrate various cassette identification systems involving either contact or non-contact between cassette 26 and control module 24. Some alternative non-contact cassette identification systems include those utilizing a magneto-resistive switch as part of the cassette identification device 42, and a magnet associated with cassette 26 as the indicia 40. The magneto-resistive switch sends a signal to the processor 52 that the resistivity induced in a current carrying conductor or semiconductor is changed by the application of the magnetic field from the magnet on cassette 26.

The cassette identifying device 42 could instead include a Hall effect sensor, with indicia 40 including a magnet. A Hall effect switch is a magnetically activated switch that uses a Hall generator, a trigger circuit, and a transistor amplifier on a silicon chip. A further alternative may include a cassette identifying device having a reed switch, with indicia 40 including a magnet. A reed switch typically has contacts mounted on ferromagnetic reads sealed in a glass tube designed for actuation by application of the magnetic field of the magnet.

Another alternative indicia identifying device 42 may include a piezoelectric switch or a capacitive switch. Further alternative embodiments may include an acoustical emitter/detector for indicia identifying device 42. Additional embodiments of indicia identifying device 42 include bar code readers or other text or printed marking readers which can read printed material on cassette 26. Laser positioning sensors may be utilized where the height of a projection extending from the base plate is measured to identify the cassette.

While the systems shown in FIGS. 3-20 identify cassettes 26 by identifying a single indicia 40 on each cassette, it is to be understood that the identification system could look for two indicia, such as two projections, for each cassette. A redundant system could still be provided in that case since the control module would request that two signals be received. Less than two or more than two would indicate an error condition. Moreover, the invention is not to be limited to three sensors. More than three, or less than three, are possible whether the systems sense the presence of one indicia, the absence of one indicia, or variations in the number of indicia sensed, such as zero, one, two, three, etc. corresponding to the number of sensors provided and the possible combinations thereof.

Figure 21:
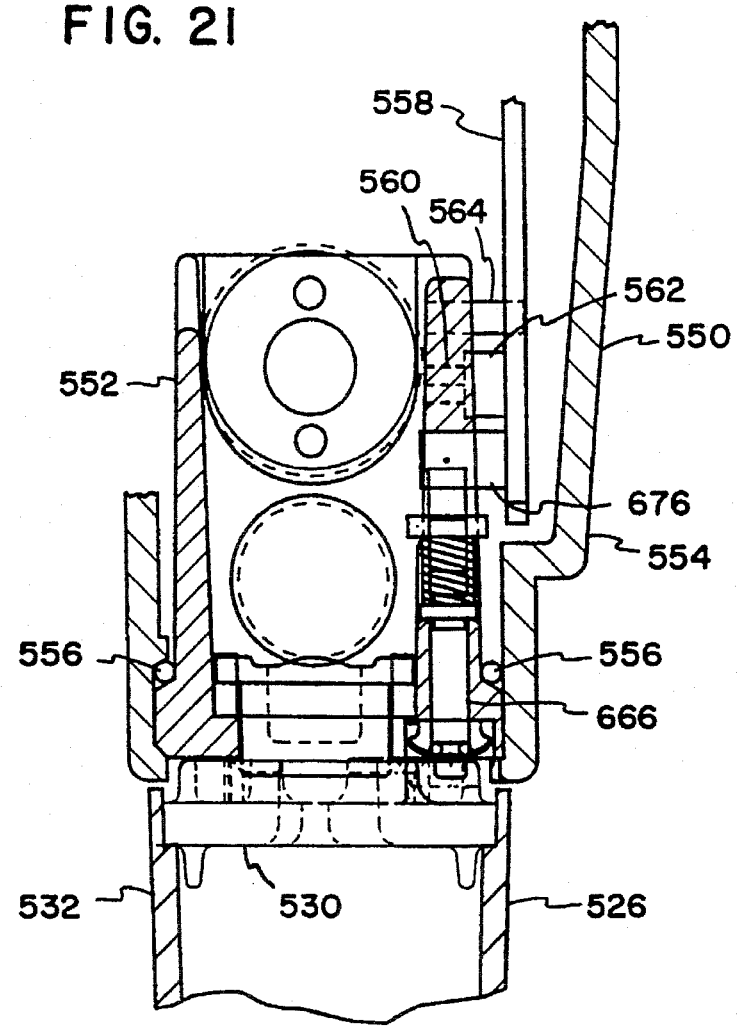
FIGS. 21–29 illustrate one preferred cassette identification system.
Figure 22:
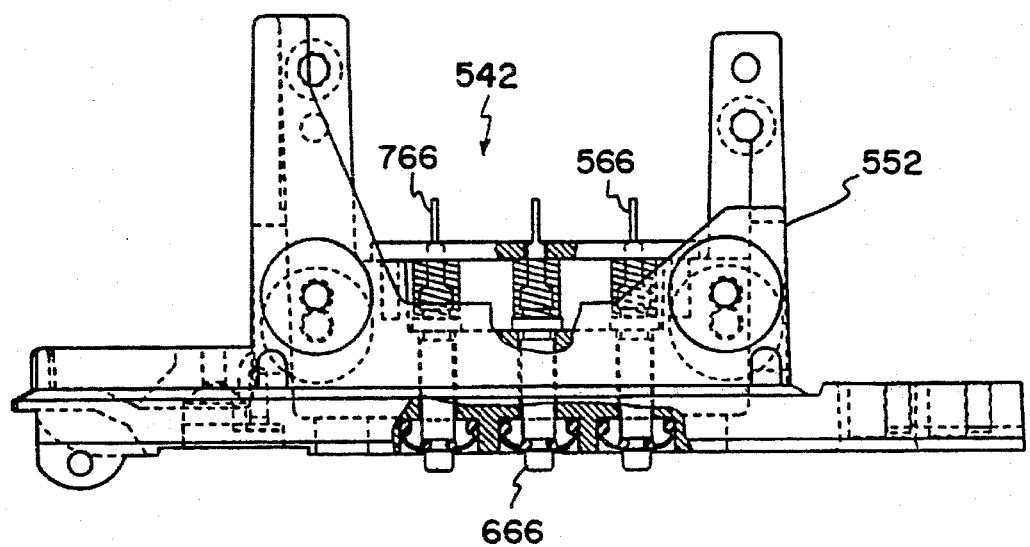
Figure 23:
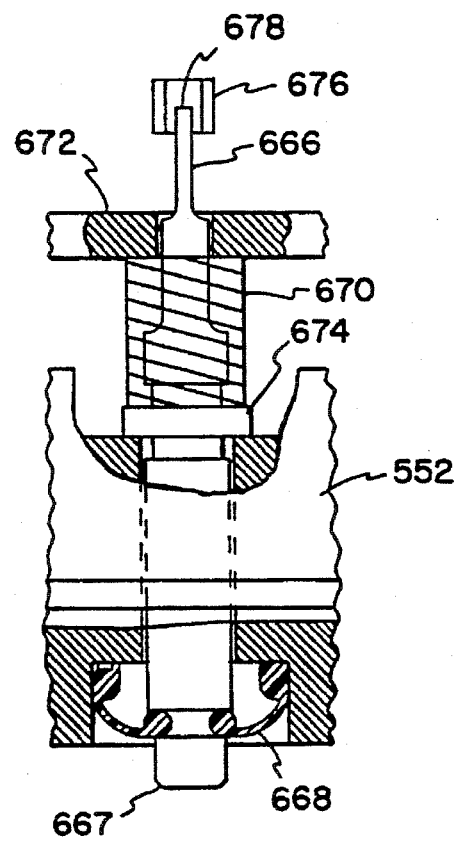
Figure 24:
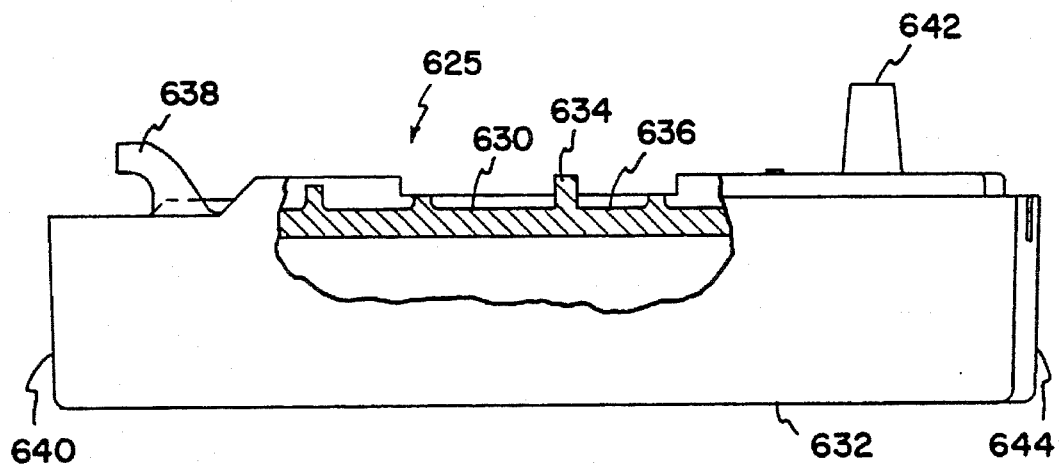
Figure 25:
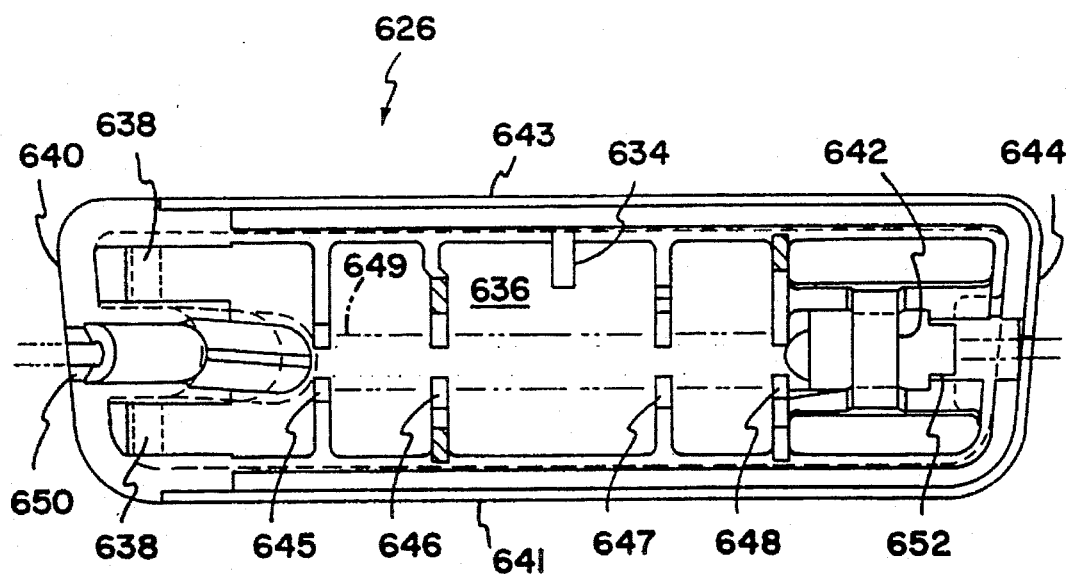
Figure 26:
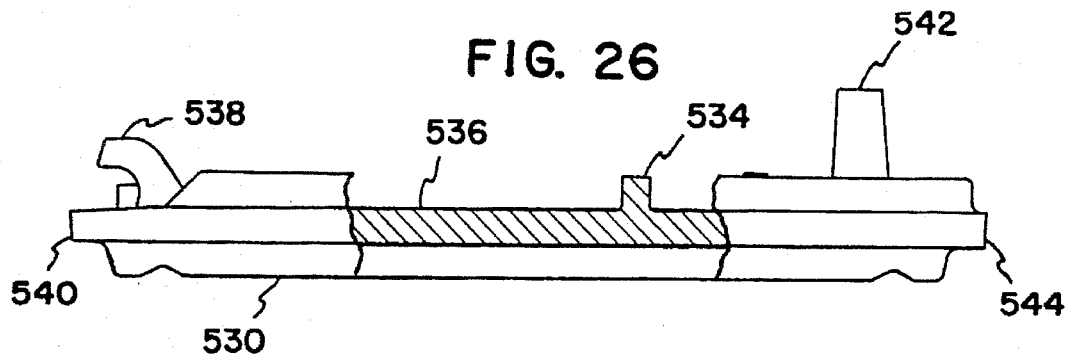
Figure 27:
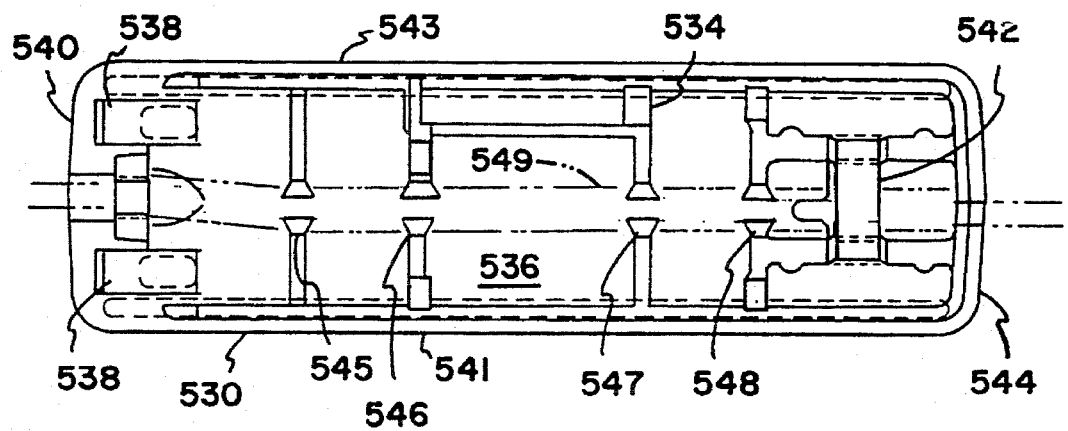
Figure 28:
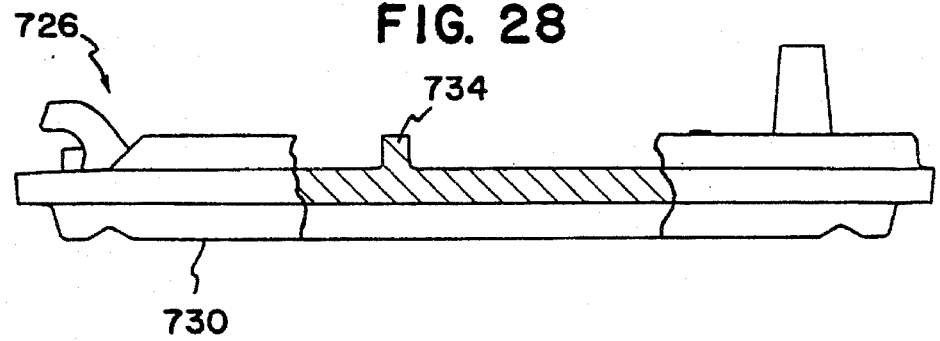
Figure 29:
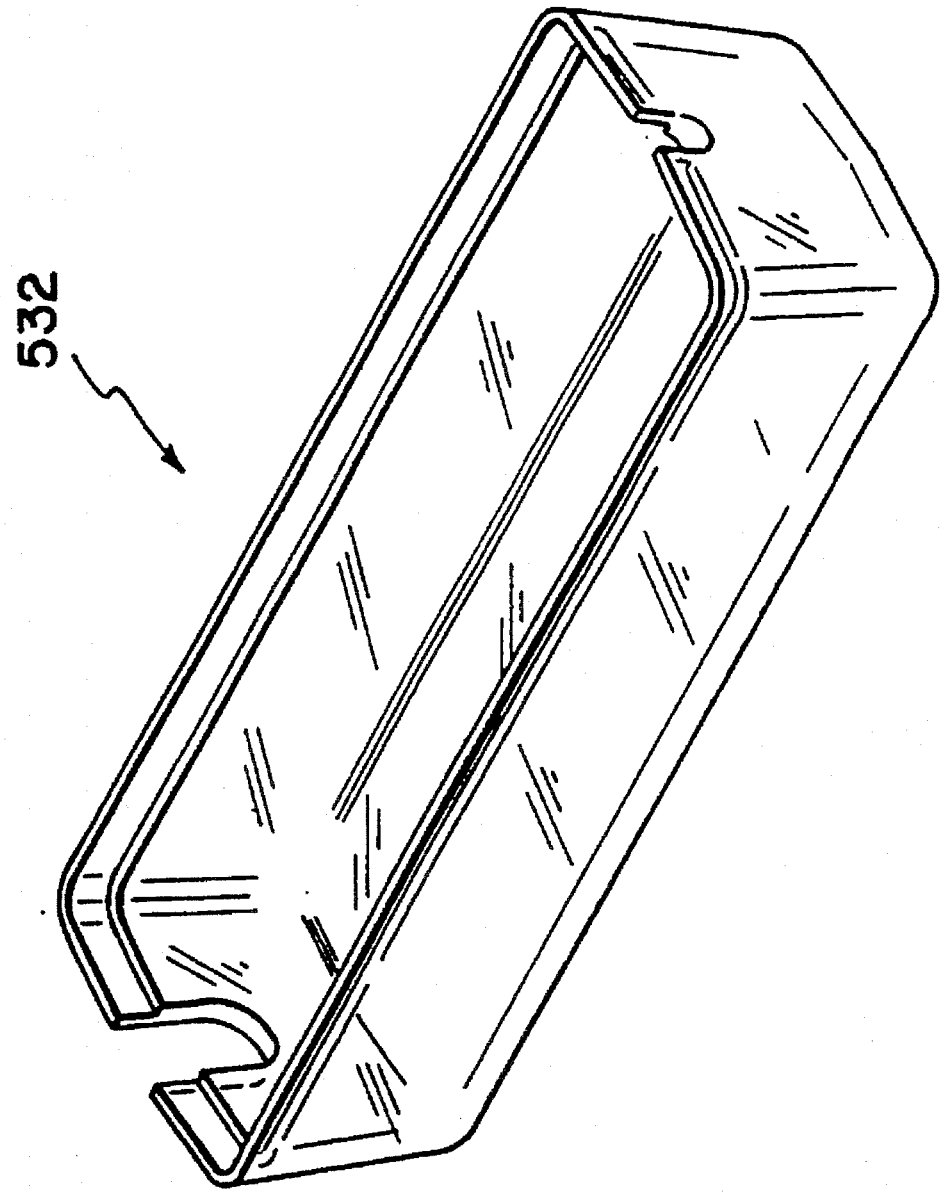

Referring now to FIGS. 21-29, a preferred cassette identification system is shown. FIGS. 21-23, 26, 27 and 29 show a preferred control module 550, a preferred cassette sensing mechanism 542, and a first preferred cassette 526. FIG. 21 shows first cassette 526 assembled and mounted to control module 550. FIGS. 26, 27 and 29 show various side and top views of a base plate 530 of cassette 526, and a perspective view of a base 532 of cassette 526. FIG. 22 shows only chassis 552 with the various plungers mounted thereto. FIG. 23 is an enlarged view of a portion of chassis 552 with a slotted optical sensor 676 shown in its relative position to plunger 666. FIGS. 24 and 25 show a second cassette 626 in side and top views, respectively. FIG. 28 shows a third cassette portion, base plate 730, useable with base 532 of FIG. 29 to form third cassette 726 in a similar manner as first cassette 526. The second and third preferred cassettes 626 and 726 are also part of the preferred cassette identification system. Cassette sensing mechanism 542 can distinguish between cassettes 526, 626, 726. For example, first cassette 526 can have a first pumping volume per activation, i.e., 50 μl. Second cassette 626 can have a second pumping volume per activation, different from the first pumping volume, i.e., 100 μl. It is critical for control module 550 to know how much fluid is pumped per activation of the pumping mechanism to deliver the desired drug therapy. In an improper drug therapy, either too much or too little drug can be harmful, and in some cases, fatal.

While variations of cassette identification systems have been shown in FIGS. 1-20, and described above, the cassette identification system of FIGS. 21-29 is preferred. As shown in FIG. 21, first cassette 526 includes base plate 530 and base 532 mounted thereto. Base plate 530 is shown in greater detail in FIGS. 26 and 27. Base 532 is shown in greater detail in FIG. 29. Base plate 530 is adhesively attachable to base 532. Alternatively, a snap arrangement can be provided. In a further alternative, a snap arrangement and adhesive can be utilized. In a further alternative, base plate 530 and base 532 can be integrally formed as a single unit, such as by molding in the case of plastics.

Control module 550 includes a chassis 552 and an outer housing 554. A seal 556 seals between chassis 552 and housing 554. A component board 558 is mounted to chassis 552 via screws 560, spacers 562, and alignment pins 564. A first plunger 566 is reciprocally mounted to chassis 552. Second plunger 666 and third plunger 766 are also reciprocally mounted to chassis 552. Plungers 566, 666, 766 are similarly configured and operated. FIG. 23 shows second plunger 666 in greater detail. A seal 668 seals an end of second plunger 666. A spring 670 biases second plunger 666 to the position shown in FIGS. 21–23. A bezel 672 traps spring 670 in position as shown. A flange 674 limits second plunger 666 from being pulled downwardly out of the position shown in FIGS. 21–23. During operation, a projection extending from the cassette engages end 667 and causes upward movement of second plunger 666 such that end 678 of second plunger 666 moves into a new position relative to slotted optical sensor 676, which causes a signal to be sent to the processor of control module 550 that a projection has been sensed.

First plunger 566 and third plunger 766 are provided for sensing additional projections. In particular, first plunger 566 engages projection 534 extending from the main surface 536 of base plate 530 of first cassette 526. Second plunger 666 engages second projection 634 extending from main surface 636 of base plate 630 of second cassette 626. Third plunger 766 engages projection 734 extending from base plate 730 of third cassette 726. In this manner, control module 550 can identify at least three different cassettes 526, 626, 726.

Referring in particular to FIGS. 21, 26, 27 and 29, base plate 530, and base 532 are shown. Extending from main surface 536 are a pair of hooks 538 adjacent to a first transverse end 540. A loop 542 extends from the main surface 536 adjacent to a second transverse end 544. A plurality of tube guide pairs 545, 546, 547, 548 extend from main surface 536 and are spaced apart to receive a flexible tube, in a general direction parallel to first and second longitudinal sides 541, 543 of main surface 536. In FIG. 26, background portions have been removed behind the cross-sectional portion for clarity. In FIG. 27, a tube 549 is shown in dashed lines.

Referring now to FIGS. 24 and 25, base plate 630, and base 632 are shown in greater detail. Extending from main surface 636 are a pair of hooks 638 adjacent to a first transverse end 640. A loop 642 extends from main surface 636 adjacent to a second transverse end 644. A plurality of tube guide pairs 645, 646, 647, 648 extend from main surface 636 and are spaced apart to receive a flexible tube, in a general direction parallel to first and second longitudinal sides 641, 643 of second cassette 666. In FIG. 25, a tube 649 is shown in dashed lines.

As shown by a comparison of FIGS. 24 and 25 with FIGS. 26 and 27, projection 534 is in a different relative location to projection 634 in a direction parallel to longitudinal sides 641, 643. It should also be noted that FIGS. 24 and 25 illustrate the integral construction between base plate 630 and base 632. Cassette 626 also includes features for more accurate centering of tube 649 which is larger than tube 549, such as the V-shaped passages provided in connection with guide pairs 645, 646, 647, 648.

Also, cassette 626 includes clip features for releasably gripping tube 649 to provide a mechanical hold down during adhesive attachment of tube 649 to cassette 646. In particular, first clip 650 and second clip 652 provide hold down of tube 649 to cassette 626. First clip 650 and second clip 652 hold the tube in place during assembly, allowing the adhesive to set up without the need for special clamps or external fixtures.

Referring now to FIG. 28, third cassette 726 is shown. With respect to FIG. 28, a base plate 730 is illustrated. Base 532 shown in FIG. 29 is useable with base plate 730 shown in FIG. 28. Projection 734 is in a different relative location on base plate 730 than projection 534 of base plate 530 and projection 634 of base plate 630. Projection 734 can be indicative of a different cassette property to differentiate cassette 726 from cassettes 626, 526. For example, cassette 726 may include an indication that an air filter is present to identify to the control module when the cassette is utilized with a reservoir including an in-line air filter.

The cassette identification system of FIGS. 21–29 incorporates features of embodiments described in various of FIGS. 1, 1A, 2, 14, 15, 18, and 20, for example. The system of FIGS. 21–29 may be advantageous over mechanical switches, such as microswitches, since little or no emphasis need be placed on overtravel, individual adjustment, arcing problems, and mechanical wearing of the switch. Inductive, magnetic, or reflective systems may require the placement of an additional element on the cassette during manufacture. A projection as in FIGS. 21–29 can be integrally formed on the cassette during manufacture, possibly simplifying manufacture. Force sensitive resistors may be prone to problems due to typical range of necessary movement and the typical tolerances of the disposable cassettes. Also, the plastics associated with the FSR or its spring may be subject to creep problems over time, possibly further complicating the range of motion and tolerance problem. Make or break switches where the contacts are mounted to a moveable plunger, for example, may be prone to failure due to the failure of the contact points, such as due to pitting or corrosion, or due to the components getting stuck open or closed.

Reciprocally mounted plungers and slotted optical sensors are useful to solve some of the above possible problems and other problems with cassette identification systems. However, it is to appreciated that in some instances the use of microswitches, FSR's, inductive switches, magnetic switches, reflective elements, moving contacts, or other systems noted above may be desireable.

While the present invention has been described in connection with the preferred embodiments thereof, it will be understood many modifications will be readily apparent to those skilled in the art, and this application is intended to cover any adaptations or variations thereof. It is intended this invention be limited only by the claims and equivalents thereof.

What is claimed is:

1. A pump apparatus comprising:
    a control module including a processor and a pumping mechanism for pumping fluid through a fluid tube;
    a base plate selectively mounted to the control module;
    a fluid tube positioned between the base plate and the pumping mechanism of the control module;
    a light emitter associated with the control module for directing light toward the base plate;
    a light reflector associated with the base plate for reflecting light toward the control module;
    a light receiver associated with the control module for receiving light reflected from the light reflector of the base plate;
    means associated with the light receiver for sending a signal to the processor indicative of the light being sensed.

2. The pump apparatus of claim 1, wherein the light reflector includes a prism arrangement.

3. The pump apparatus of claim 2, further comprising a second light receiver associated with the control module.

4. The pump apparatus of claim 1, wherein the light reflector includes a light reflective patch.

5. The pump apparatus of claim 4, further comprising a second light emitter and a second light receiver associated with the control module.

6. A base plate for use with a control module having a light emitter and a light receiver comprising:
- a body having a main surface facing in a first direction and including first and second longitudinal sides, and first and second transverse ends;
- a pair of hooks extending from the main surface adjacent to the first transverse end;
- a loop extending from the main surface adjacent to the second transverse end;
- a plurality of tube guide pairs extending form the main surface and spaced apart to receive a flexible tube in a direction generally parallel to the first and second longitudinal sides; and
- a light reflector associated with the body for reflecting light from the light emitter of the control module toward the light receiver of the control module.

7. A pump control module comprising:
- a housing including a processor, a pumping mechanism extending from the housing for pumping fluid through a fluid tube, and a mounting mechanism for selectively mounting a base plate to the housing;
- a light emitter mounted to the housing for directing light toward the base plate, the light emitter facing in a first direction; and
- a light receiver mounted to the housing for receiving light reflected from the light reflector of the base plate, the light receiver facing in the first direction, the light receiver sending a signal to the processor indicative of light being sensed.

8. A method for pumping fluid comprising the steps of:
- providing a control module having a pumping mechanism;
- providing a fluid reservoir having a base plate;
- providing a first sensor for electronically signalling to the control module that a predetermined base plate has been interconnected to the control module;
- interconnecting the base plate to the control module;
- directing light from the control module toward the base plate after the base plate is interconnected to the control module;
- reflecting the light from the base plate in a direction back toward the control module;
- after the reflected light has been sensed by the first sensor, sending an electronic signal to the control module that a predetermined base plate has been interconnected to the control module; and
- pumping fluid with the pumping mechanism.

9. The method of claim 8, further comprising the steps of:
- providing a second sensor;
- sensing reflected light with the second sensor;
- before the step of sending an electronic signal to the control module that a predetermined base plate has been interconnected to the control module, comparing the amount of light sensed by the first sensor and the second sensor; and
- based on the results of the comparing step, creating a signal for sending to the control module identifying the base plate as a particular predetermined base plate.

10. The method of claim 8, further comprising the step of modulating the light directed from the control module.

* * * * *

UNITED STATES PATENT AND TRADEMARK OFFICE
CERTIFICATE OF CORRECTION

PATENT NO. : 5,531,698

DATED : July 2, 1996

INVENTOR(S) : Olsen

It is certified that error appears in the above-identified patent and that said Letters Patent is hereby corrected as shown below:

On the cover page, Section (54), and in Column 1, in the title, "FORDRUG" should read -- FOR DRUG--.

In claim 6, Column 15, line 14, "form" should read --from--.

Signed and Sealed this

Nineteenth Day of November, 1996

Attest:

BRUCE LEHMAN

*Attesting Officer*     *Commissioner of Patents and Trademarks*